United States Patent [19]

Humphrey et al.

[11] Patent Number: 4,583,973

[45] Date of Patent: Apr. 22, 1986

[54] VISCOUS FLUID TIMED INFUSION DEVICE

[76] Inventors: Robert Humphrey; Carl Biro, both of 2002 Utopia Parkway, Whitestone, N.Y. 11357

[21] Appl. No.: 599,076

[22] Filed: Apr. 11, 1984

[51] Int. Cl.$^4$ .............................................. A61M 5/20
[52] U.S. Cl. .................................. 604/135; 604/207; 604/218
[58] Field of Search ............... 604/134, 135, 191, 207, 604/208, 218, 224, 228; 221/16; 222/340, 341

[56] References Cited

U.S. PATENT DOCUMENTS

| | | |
|---|---|---|
| 2,725,877 | 12/1955 | Reiter et al. .................... 604/224 |
| 3,515,130 | 9/1967 | Tsujino . |
| 3,605,745 | 9/1971 | Hodosh . |
| 3,880,163 | 4/1975 | Ritterskamp .................... 604/136 |
| 3,945,379 | 3/1976 | Pritz et al. . |
| 3,945,383 | 3/1976 | Bennett et al. . |
| 3,949,748 | 4/1976 | Malmin .......................... 604/135 |
| 4,056,102 | 11/1977 | Levinson et al. ............... 604/135 |
| 4,103,684 | 8/1978 | Ismach . |
| 4,150,672 | 5/1979 | Whitney et al. . |
| 4,267,836 | 5/1981 | Whitney et al. . |
| 4,300,554 | 11/1981 | Hessberg et al. . |

*Primary Examiner*—John Doll
*Assistant Examiner*—Glenn A. Caldarola
*Attorney, Agent, or Firm*—Pennie & Edmonds

[57] ABSTRACT

A viscous fluid timed infusion device having a cylindrical housing having an orifice in one end. A plunger is movable in the housing and spring means are operatively positioned in the housing to urge the plunger towards the orifice. A viscous fluid timing device controls rate of movement of the plunger towards the orifice.

8 Claims, 5 Drawing Figures

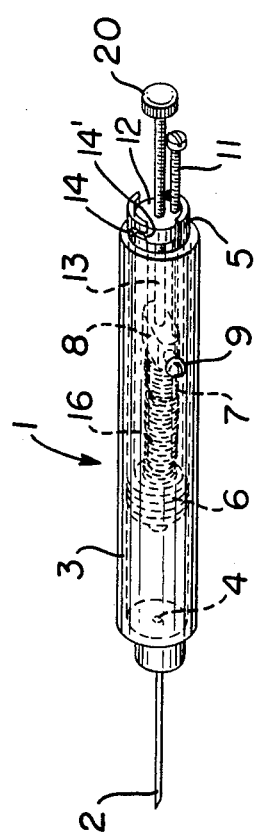
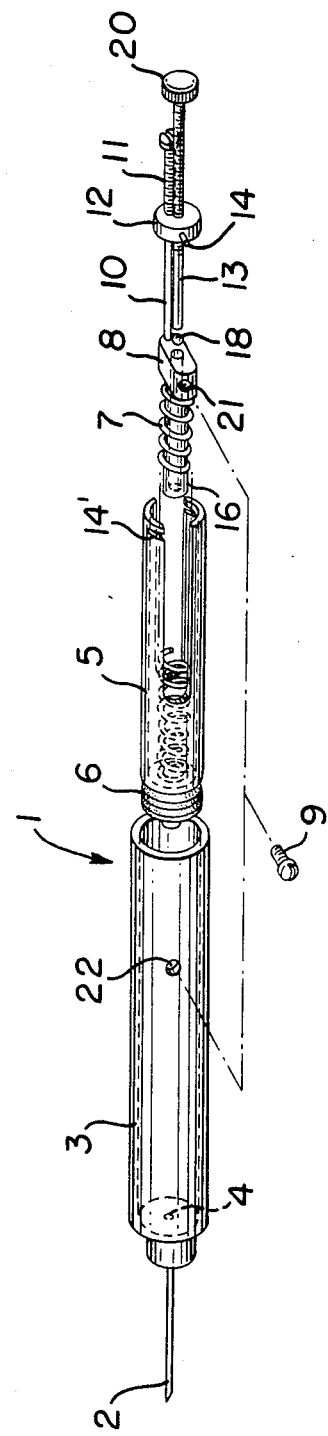

VISCOUS FLUID TIMED INFUSION DEVICE

TECHNICAL FIELD

This invention relates to a viscous fluid timed infusion device and more particularly to a portable metering syringe by which medicine may be continuously injected into a patient over a predetermined period of time.

BACKGROUND OF THE INVENTION

Treatment of a number of medical disabilities, as for example diabetes, requires continuous application of medication to replace a lost body function. This is often accomplished by a continuous injection by means of a syringe of a medication directly into the blood stream of a patient over a predetermined period of time which often may extend from a few hours to a number of days. In order that the patient not be immoblized, it is desirous that the syringe be of a portable type such that it may be strapped to the patient. This requires that the syringe be small, and from an economic viewpoint, be easily assembled of conveniently manufactured parts.

It is a further requirement in such devices that the dosage of medication be accurately metered to assure that the correct amount of medication is administered over a set predetermined amount of time. Electric motor driven devices have been proposed but such devices are subject to problems of variations in charges of batteries necessary to drive the devices. Spring motor clockwork devices have been proposed but these usually result in relatively large devices which tend to impede mobility of a patient.

Further it is desirable that such devices be capable of having their rate of metering easily changed to accommodate varying rates of application of dosages.

It is therefore an object of the invention to provide for a viscous fluid timed infusion device that is small so as to be easily strapped to a patient in order to keep any immobilization of the patient to a minimum.

It is a further object of the invention to provide for a syringe which is easy to manufacture and assemble and which at the same time provides a highly accurate device for metering application of medication over a predetermined period of time.

It is a still further object to provide for a timed infusion device by which the rate of application of dosage may be easily varied to accommodate various treatments.

GENERAL DESCRIPTION OF THE INVENTION

Broadly a viscous fluid timed infusion device constructed according to the invention comprises a cylindrical main housing having an orifice at one end adapted to contain a medication in fluid form. A main plunger sealingly engages the inner side walls of the main housing and is slidable therein such that when the plunger moves towards the orifice, medication is forced out of the orifice. A main spring means is operatively positioned between the main plunger and the main housing to urge the plunger towards the orifice. A viscous fluid timing device controls rate of movement of the plunger towards the orifice such that the rate of application of the medication is controlled.

The timer device preferably comprises a cylindrical auxiliary housing having a closed end and an opposite end having an opening therein with the housing containing a viscous fluid. A metering valve piston is movable in the auxiliary housing and is operatively connected to the main plunger such that when the main plunger moves towards the orifice under the influence of the main spring, the piston will move in the auxiliary cylinder towards the closed end. Leakage of viscous fluid around the edges of the piston controls rate of movement of the piston towards the closed end of the auxiliary housing and consequently the rate of movement of the main plunger in the main housing since the main plunger is operatively connected to the piston.

The metering piston preferably comprises a ball mounted for movement within the auxiliary cylindrical housing. Variations in leakage, and thus in rate of movement of the ball in the auxiliary housing, can be regulated by changing ball sizes.

An auxiliary spring is positioned between the closed end of the auxiliary housing and the ball to urge the ball towards the opening so that the ball remains in its initial position. The opening is sealed with metal foil which is ruptured upon initiation of the device. A plunger rod which ruptures the foil is operatively connected with the main plunger and is adapted to engage the ball to urge it against the force of the auxiliary spring to move the ball towards the closed end of the auxiliary housing.

Preferably the plunger rod is initially spaced from the ball and regulation means are provided for varying this spacing. The spacing allows the main plunger to move independently of the ball until the plunger rod contacts the ball. This independent movement of the main plunger will move medication through the orifice and through a hollow needle to expel air from the needle prior to injection of the needle into a patient. The spacing is made variable to accommodate different length needles or tubings to which the device may be connected.

The device also includes a release means which in one position locks the main plunger with respect to the main housing and which in a second position allows relative movement between the two.

Preferably the auxiliary housing is positioned concentrically within the main housing to reduce overall space requirements. It could however be positioned exteriorly of the main housing.

The housings and plungers may conveniently be molded from glass so as to reduce expense of manufacture and which may then allow the device to be discarded after use.

BRIEF DESCRITION OF THE DRAWINGS

FIG. 2 is a side view of the device of FIG. 1 shown in assembled form;

FIG. 3 is an exploded view of the device of FIG. 2 shown in disassembled form;

DESCRIPTION OF THE PREFERRED EMBODIMENT

Figure 1:
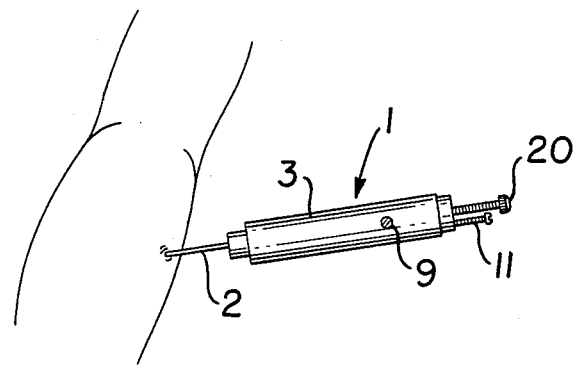
FIG. 1 is a view of a viscous fluid timed infusion device constructed according to the invention as applied to a patient.

Referring to FIG. 1 there is illustrated a viscous fluid timed infusion device 1 constructed according to the invention as applied to an arm of a patient. Normally the device would be strapped directly to the arm so as not to impede mobility of the patient. Of course the device could be connected to other portions of the body and if necessary the needle 2 could be connected by flexible tubing to the device further adding to the areas of placement of either a needle or the device to the body.

Referring to FIGS. 2 and 3, it is seen that the device comprises a main cylindrical housing 3 having an orifice 4 at one end with the opposite end being open. A hollow main cylindrical plunger 5 is slidable in the housing 3 and has rubber sealing rings 6 on one end thereof such that the plunger sealingly engages the inner side walls of the housing 3.

A main compression spring 7 is operatively positioned in the plunger 5 between the end of the plunger containing the rings 7 and a spring stop 8 which is held in the housing 3 by means of a set screw 9.

The stop 8 has a tie bar 10 rotatably connected thereto which is threaded with a cap 12. Cap 12 in turn has a plunger rod 13 which threads with cap 12 so as to be moved in a longitudinal direction with respect to the cap. A pin 14 on the side of cap 12 is adapted to engage a slot 14 in the main plunger when it is assembled into the main cylindrical housing 3 as explained hereafter in greater detail.

Figure 4:
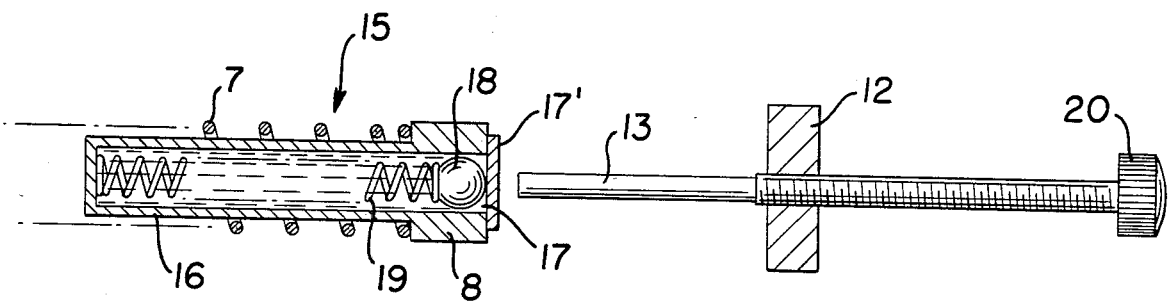
FIG. 4 is a schematic view of a poriton of the structure of the device of FIG. 2 illustrating a timing device prior to use.
Figure 5:
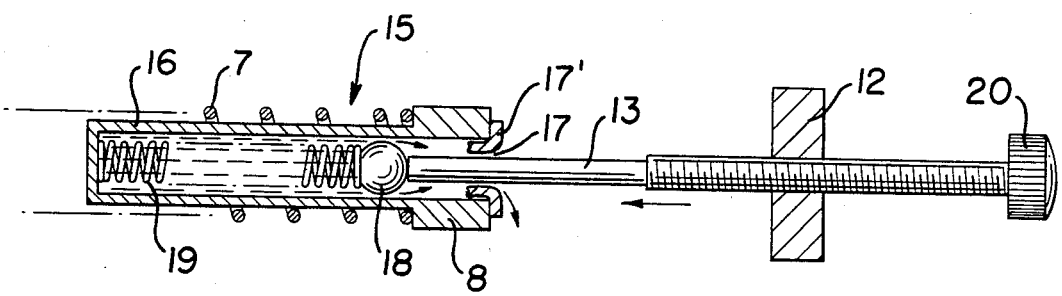
FIG. 5 is a view similar to FIG. 4 illustrating the timing device during use.

Referring to FIGS. 4 and 5 there is shown a viscous fluid timing device 15 as used with the infusion device. The timing device comprises an auxiliary cylinder 16 closed at one end and having an opening 17 in an opposite end which is sealed by a metal foil 17'. The cylinder 16 may as shown be integral with the spring stop 8 to form a part thereof or it could form a separate part joined to the stop in which event the stop would have a hole in line with an opening in the end of the auxiliary cylinder.

The cylinder 16 contains a viscous fluid as well as a ball 18, which as shown in FIG. 4 is urged by an auxiliary compression spring 19 towards the opening 17.

The ball 18 is adapted to be engaged by the plunger rod 13 through the opening 17 after it ruptures the foil 17' to force the ball towards the closed end of the auxiliary housing 16 as shown in FIG. 5. As the ball moves towards the closed end the viscous fluid leaks around the sides of the ball. It is apparent that the rate of movement of the ball towards the closed end is dependent on the rate of leakage of the fluid about the sides of the ball. Metering devices of this type are known as LAOD devices which is an acronym for Liquid, Annular, Orifice, Dashpot. It can be seen that the rate of leakage, and thus rate of movement of the plunger rod 13 can be varied by replacing ball 18 with balls of different diameters.

The auxiliary cylinder 16 is preferably positioned coaxially within the plunger as shown in FIG. 3.

The rod 13 is initially spaced a predetermined distance from the ball 18, the spacing being regulated to a predetermined amount by rotating the regulating knob 20 on the end of the rod 13 to move the end of the rod either away from or towards the ball. The amount of spacing is determined by the amount the main plunger must move in the main housing to expel medication from the housing through the orifice 4 to completely expel air from the needle 2 and any associated tubing before the needle is injected into the patient.

The infusion device 1 is assembled as follows. The spring stop 8 including the auxiliary housing 16 and spring 7 as well as cap 12, tie bar 10 and plunger rod 13 are pushed into the hollow main plunger 5 compressing the main spring 7 until the pin 14 is opposite the slot 15. At this point the tie bar 10 and rod 13 are turned so that the pin 14 is locked into the slot 15. The main housing 3 is then filled with a predermined amount of fluid medication after which the plunger 5 is slid into the housing until a threaded hole 21 in the stop is opposite a hole 22 in the side of the main housing. A set screw 9 is then threaded into hole 21 to lock the stop 8 as well as the timing device 15 in the main housing.

The operation of the infusion device is as follows. The regulating means comprising the knob 20 is turned to pre-set the distance from the end of the rod 13 to the ball 18 to allow sufficient movement of the main plunger 5 in the main housing independent of the timing device 15 in order to expel any air that may be contained in the needle and any associated tubing. When it is desired to commence treatment, the release means comprising the rotatable threaded tie bar is turned to unscrew the tie bar with respect to the cap 12. This then allows the main plunger to quickly move towards the orifice 4 to expel air from the needle and any associated tubing after which the needle is inserted into the patient. Movement of the plunger towards the orifice also moves the cap 12 and rod 13 in the direction of the orifice until the end of the rod engages the ball 18. After this point the rate of movement of the main plunger, cap 12 and plunger rod 13 is determined by the rate of leakage of the viscous fluid around the edges of the ball 18.

It is seen that an infusion device as described comprises a minimum of parts which, because of the construction used, can be easily shaped, as for example, by molding from glass. This in turn means that the device can be economically manufactured so that it can be to be disposed of after usage.

Further it is seen that the rate of infusion can be easily varied by merely changing size of the ball in an existing auxiliary housing where the housing forms part of the stop 8 or by connecting a different auxiliary housing ball unit to the stop 8.

The device as described is approximately the same size and shape as conventional syringes allowing it to be easily attached to a portion of a patients body.

While the invention has been described in connection with syringes, it is apparent that the infusion device is applicable for use in any situation in which it is desired to obtain an accurate metering of a liquid over a predetermined period of time.

We claim:

1. A viscous fluid timed infusion device comprising a cylindrical main housing, an orifice in one end of said housing, a plunger sealingly engaging inner side walls of said main housing and slidably therein, main spring means operatively positioned between said main housing and said plunger urging said plunger toward said orifice to force a fluid in said cylinder through said orifice, and a viscous fluid timing device independent of said oriface and operatively connected to said plunger for controlling rate of movement of said plunger towards said orifice in response to flow of viscous fluid through said timing device.

2. A viscous fluid timed infusion device according to claim 1 having in addition locking release means which in one position locks said main plunger from movement within said main cylindrical housing and which in a second position allows said main plunger to move towards said orifice under the force of said main spring.

3. A viscous fluid timed infusion device comprising a cylindrical main housing, an orifice in one end of said housing, a plunger sealingly engaging inner side walls of said main housing and slidable therein, main spring means operatively positioned between said main housing and said plunger urging said plunger towards said orifice to force a fluid in said cylinder through said orifice, and a viscous fluid timing device for controlling rate of movement of said plunger towards said orifice, said viscous fluid timing infusion device comprising a cylindrical auxiliary metering valve housing closed at one end and having an opening at its opposite end containing a viscous fluid, a metering valve piston movable in said auxiliary metering valve housing and operatively connected to said plunger whereby leakage of viscous fluid in said auxiliary metering valve housing about said piston controls rate of movement of said piston in said auxiliary metering valve housing.

4. A viscous fluid infusion device according to claim 3 wherein said cylindrical auxiliary metering valve housing is positioned concentrically within said main cylindrical housing.

5. A viscous fluid timed infusion device according to claim 3 wherein said metering valve piston comprises a ball movable in said auxiliary metering valve housing.

6. A viscous fluid timed infusion device according to claim 5 having in addition auxiliary spring means for urging said ball out of said auxiliary metering valve housing towards said opening.

7. A viscous fluid timed infusion device according to claim 6 having in addition a plunger rod operatively connected to said plunger adapted to contact said ball to move it against the force of said auxiliary spring means when said main plunger is moved towards said orifice.

8. A viscous fluid timed infusion device according to claim 7 having in addition regulation means for varying spacing between an end of said plunger rod and said ball whereby said main plunger may move towards said orifice for a predetermined distance independent of any movement of said ball.

* * * * *